United States Patent [19]

Ohkuma et al.

[11] Patent Number: 4,952,572

[45] Date of Patent: Aug. 28, 1990

[54] BU-3420T ANTIFUNGAL ANTIBIOTIC

[75] Inventors: Hiroaki Ohkuma, Tokyo; Masataka Konishi, Kanagawa; Kiyoshi Matsumoto, Kawaguchi; Toshikazu Oki, Yokohama; Yutaka Hoshino, Tokyo, all of Japan

[73] Assignee: Bristol-Myers Company, New York, N.Y.

[21] Appl. No.: 434,756

[22] Filed: Nov. 13, 1989

Related U.S. Application Data

[62] Division of Ser. No. 208,330, Jun. 10, 1988, Pat. No. 4,916,055.

[51] Int. Cl.$^5$ ............................................ A61K 31/505
[52] U.S. Cl. ................................................... 514/279
[58] Field of Search ................ 514/229; 435/169, 170; 424/123

[56] References Cited

U.S. PATENT DOCUMENTS

| | | | |
|---|---|---|---|
| 4,530,835 | 7/1985 | Bunge et al. | 435/169 |
| 4,533,547 | 8/1985 | Omura et al. | 435/169 |
| 4,578,271 | 3/1986 | Kiyoto et al. | 435/169 |
| 4,661,353 | 4/1987 | Wilton et al. | 424/123 |
| 4,675,187 | 6/1987 | Konishi et al. | 435/170 |

Primary Examiner—Douglas W. Robinson
Assistant Examiner—Kevin Weddington
Attorney, Agent, or Firm—David M. Morse

[57] ABSTRACT

The novel antitumor antibiotic designated herein as BU-3420T is produced by fermentation of *Micromonospora chersina* strain M956-1 (ATCC 53710). BU-3420T and its triacetate derivative possess antibacterial and antifungal activity and also inhibit the growth of mammalian tumors such as P388 leukemia in mice.

2 Claims, 2 Drawing Sheets

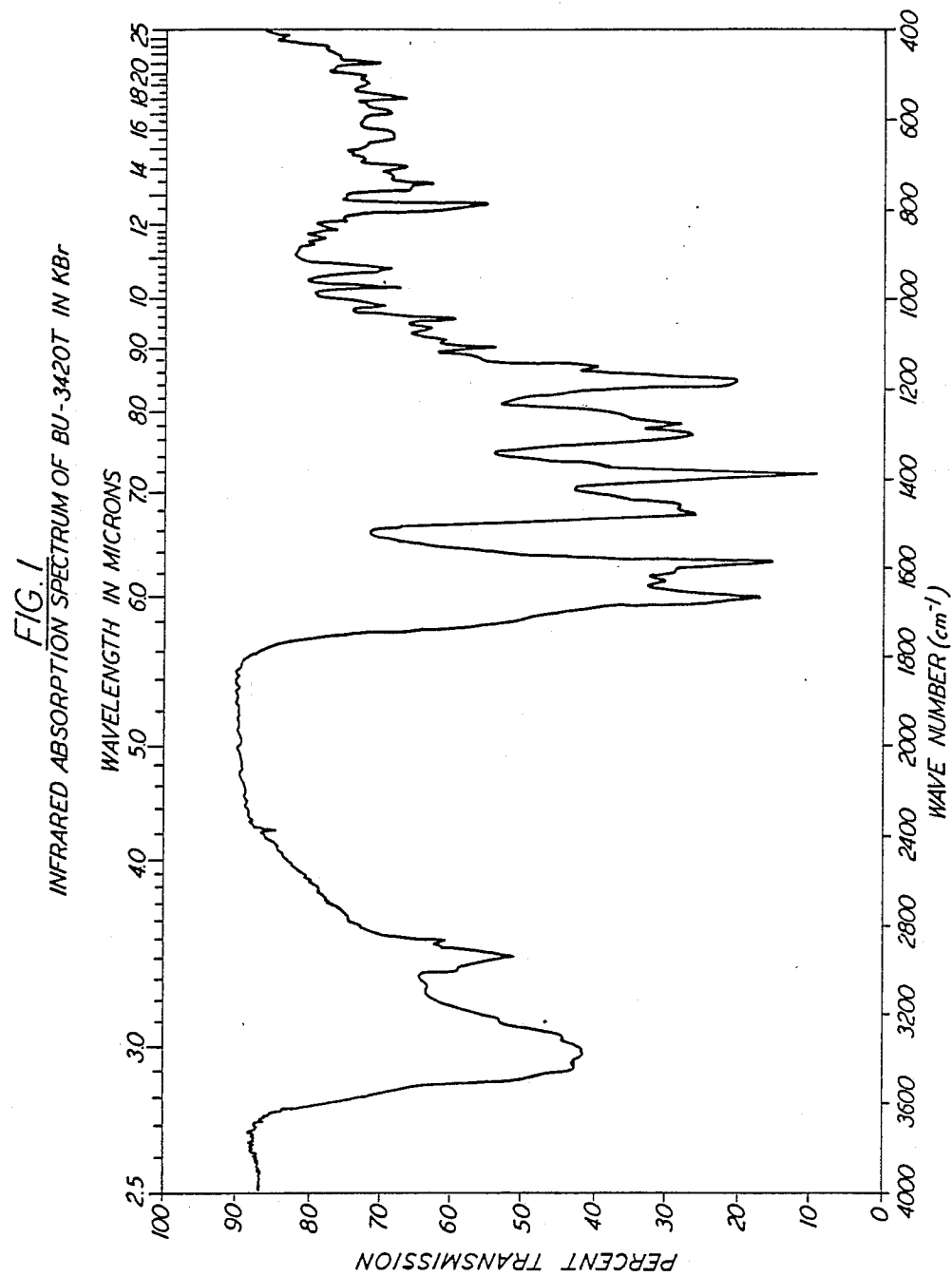

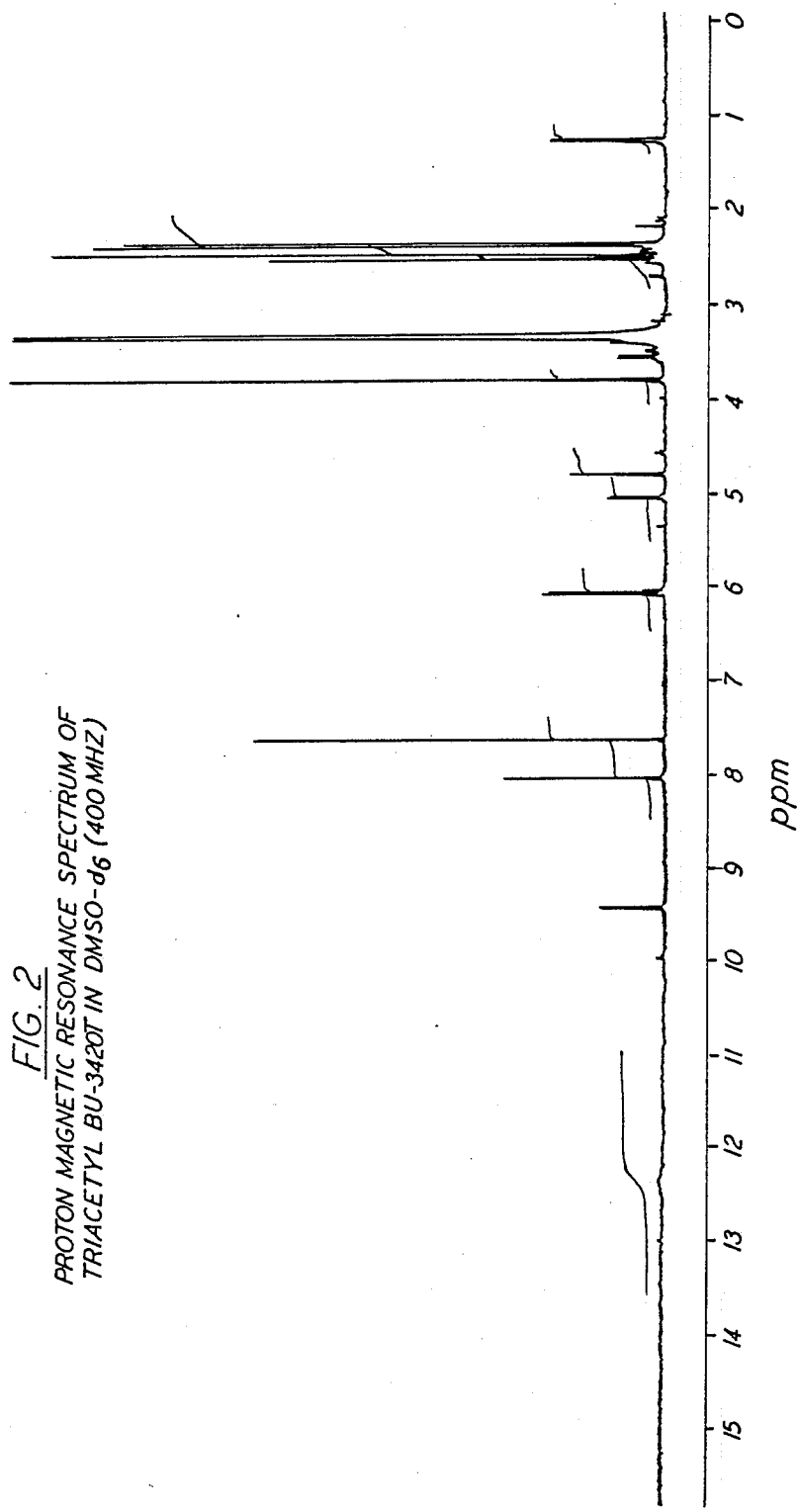

BU-3420T ANTIFUNGAL ANTIBIOTIC

This is a division of our prior co-pending application Ser. No. 208,330 filed Jun. 10, 1988, U.S. Pat. No. 5,916,055.

BACKGROUND OF THE INVENTION

1. Field of the Invention

This invention relates to a novel antibiotic compound designated BU-3420T and its triacetate derivative. Both compounds possess antibacterial, antifungal and antitumor activities.

2. Description of the Prior Art

Elucidation of the structure of BU-3420T revealed that it contained a conjugated di-yne moiety. This unusual functionality was recently discovered in the esperamicins (J. Am. Chem. Soc. 10 3462–3464, 1987) and calichemicins (J. Am. Chem. Soc. 10 3466–3468, 1987) extraordinarily potent antitumor antibiotics produced by an *Actinomadura* strain (see U.S. Pat. No. 4,675,187) and a *Micromonospora* strain (Program and Abstracts of 26th Interscience Conference on Antimicrobial Agents and Chemotherapy, Sept. 1986, Abstract 227), respectively.

Esperamicins $A_1$ & $A_2$ are believed to be identical, respectively, to CL-1577A & B disclosed in U.S. Pat. No. to the antibiotics WS-6049A & B disclosed in U.S. Pat. No. 4,578,271. A fragment of CL-1577A or B designated CL-1577-$B_4$ is disclosed in U.S. Pat. No. 4,661,353 while fragments of esperamicins $A_1$ or $A_2$ designated BBM-1675C & D are disclosed in U. K. Published Application No. 2,179,649A.

SUMMARY OF THE INVENTION

The present invention provides the antibiotic BU-3420T and its tri-O-acetyl derivative which exhibit activity against a wide range of fungi and gram-positive, gram-negative and anaerobic bacteria. Additionally, the compounds exhibit in vitro and in vivo antitumor activity.

BU-3420T is obtained by cultivating a BU-3420T-producing strain of *Micromonospora chersina* in an aqueous nutrient medium containing assimilable sources of carbon and nitrogen under submerged aerobic conditions until a substantial amount of BU-3420T is produced by said organism in said culture medium and then recovering the BU-3420T from said culture medium. The triacetate derivative of BU-3420T may be prepared by acetylation of BU-3420T such as with acetic anhydride.

In another aspect there are provided pharmaceutical compositions useful for treating bacterial, fungal or carcinogenic infections in a mammalian host comprising an effective bacterial-inhibiting, fungal-inhibiting or tumorinhibiting amount of BU-3420T or its triacetate derivative together with a pharmaceutically effective carrier.

In a further aspect the present invention provides a method of treating bacterial or fungal infections in an animal host by administering to said host an effective antifungal or antibacterial amount of BU-3420T or its triacetate derivative, or a pharmaceutical composition thereof.

Finally the present invention provides a method of inhibiting the growth of tumors in a mammalian host by administering to said host a tumor-inhibiting amount of BU-3420T or its triacetate derivative, or a pharmaceutical composition thereof.

BRIEF DESCRIPTION OF THE DRAWINGS

FIG. 1 represents the infrared absorption spectrum of BU-3420T (in KBr).

FIG. 2 represents the proton magnetic resonance spectrum of triacetyl BU-3420T in DMSO-$d_6$ (400 MHz).

DETAILED DESCRIPTION

The BU-3420T antibiotic of the present invention is produced by fermentation of a BU-3420T-producing strain of *Micromonospora chersina*. The preferred producing organism is a novel strain of *Micromonospora chersina* designated herein as *Micromonospora chersina* strain M956-1. This strain was isolated from a soil sample collected in Gujarat State, India. A biologically pure culture of strain M956-1 has been deposited with the American Type Culture Collection (ATCC), Washington, D. C. and added to its permanent collection of microorganisms as ATCC 53710. Based on the major characteristics of strain M956-1, the strain was placed in the genus *Micromonospora*, and the comparative studies of strain M956-1 with related species indicated that this strain should be classified as a few species of the genus.

Strain M956-1 has the following properties:

Morpholoqy

Strain M956-1 forms vegetative mycelium (0.5 μm in width) which is long, well-branched and not fragmented. Aerial mycelium is not formed, but rudimentary aerial hypha is occasionally observed in some media. Single spores are born on the vegetative hyphae. Scanning electron micrographs show that the spores are spherical in shape (1.2–1.8 μm), sessile or born on short or long monopodial sporophores, and develop into cluster. Lateral pair or triplet of single spores are also seen at the tip of a sporophore. The surface of spores has short blunt spines.

Cultural Characteristics

Growth of strain M956-1 is moderate on ISP Medium No. 2, No. 4 and Bennett's agar, and poor in many media including Czapek's sucrose-nitrate agar, ISP Media Nos. 5 and 7. The color of vegetative mycelium is colorless to light orange yellow, and then turns to light olive gray or black after sporulation. Thick mass of spores are formed in ISP Medium No. 2 % Bennett's agar.

Melanoid and other diagnostic pigments are not produced. A fluorescent yellow diffusible pigment is produced in Czapek's sucrose-nitrate agar and ISP Medium No. 4 after one month at 28° C. The cultural characteristics of strain M956-1 are shown below in Table 1.

TABLE 1

Cultural characteristics of Strain M956-1 and a related species, *Micromonospora globosa*

| Medium | * | Strain M956-1 | *Micromonospora globosa* |
|---|---|---|---|
| Sucrose-nitrate agar (Czapek-Dox agar) | G | Poor | Moderate |
| | VM | Colorless to light orange yellow (70) | Light orange yellow (70) |
| | SL | Scant; olive gray (113) | Absent |
| | DP | Colorless, later light | Colorless, later light |

TABLE 1-continued

Cultural characteristics of Strain M956-1 and a related species, *Micromonospora globosa*

| Medium | * | Strain M956-1 | *Micromonospora globosa* |
|---|---|---|---|
| | | yellow (86) | orange yellow (70) |
| Tryptone-yeast extract agar (ISP No. 1) | G | Poor to moderate | Moderate |
| | VM | Light orange yellow (70) | Deep orange yellow (72) |
| | SL | Poor; grayish olive (110) | Absent |
| | DP | Grayish yellow (90) | None |
| Yeast extract-malt extract agar (ISP No. 2) | G | Good | Moderate |
| | VM | Colorless to pale yellow (89) | Deep orange (51) |
| | SL | Abundant; olive black (114) | Moderate; grayish brown (61) to dark olive brown (96) |
| | DP | Moderate olive brown (95) | None |
| Oat meal agar (ISP No. 3) | G | Poor | Poor |
| | VM | Colorless to pale orange yellow (73) | Colorless to vivid orange yellow (66) |
| | SL | Moderate; dark grayish yellowish brown (81) | Moderate; grayish yellowish brown (80) |
| | DP | None | None |
| Inorganic salts-starch agar (ISP No. 4) | G | Moderate | Moderate |
| | VM | Light orange (52) | Strong orange (50) |
| | SL | Poor; light brownish gray (63) | Absent |
| | DP | Colorless, later light yellow (86) | Colorless, later strong yellow (86) |
| Glycerol-asparagine agar (ISP No. 5) | G | Moderate | Moderate |
| | VM | Colorless | Colorless |
| | SL | Poor; dark olive brown (96) | Poor; dark grayish yellowish brown (81) |
| | DP | None | None |
| Peptone-yeast extract-iron agar (ISP No. 6) | G | Poor | Poor |
| | VM | Colorless | Deep orange yellow (69) |
| | SL | Poor; grayish yellowish brown (80) | Absent |
| | DP | None | None |
| Tyrosine agar (ISP No. 7) | G | Moderate | Poor |
| | VM | Colorless | Pale orange yellow (73) |
| | SL | Moderate; olive black (114) to black | Poor; grayish yellowish brown (80) |
| | DP | None | None |
| Glucose-asparagine agar | G | Scant | Poor |
| | VM | Colorless to pale orange yellow (73) | Colorless to light yellowish brown (76) |
| | SL | Scant; dark grayish yellowish brown (81) | Scant; grayish yellowish brown (80) |
| | DP | None | None |
| Nutrient agar | G | Poor | Moderate |
| | VM | Colorless | Deep orange (51) |
| | SL | Absent | Absent |
| | DP | Pale yellow (89) | Pale orange yellow (73) |
| Bennett's agar | G | Moderate | Moderate |
| | VM | Deep orange yellow (69) | Deep orange yellow (69) |
| | SL | Abundant; black | Poor; black |
| | DP | None | None |

Observations during incubation at 28° C. for 3 weeks.
Color and number in parenthesis follow ISC-NBC designation.
*Abbreviations: G; growth, VM; color of vegetative mycelium, SL; sporulation, DP; diffusible pigment

Physiological Characteristics

The growth temperature ranges from 18° C. to 49° C. No growth is seen at 15° C. and 50O° C. Optimal growth is observed between 37° C. and 44° C. Gelatin is liquefied and starch is hydrolyzed. NaCl tolerance is seen at 3% NaCl but not at 4% NaCl. Tyrosinase activity is negative.

The utilization of diagnostic sugars in Pridham-Gottlieb's inorganic medium is as follows: positive in L-arabinose, D-xylose, sucrose, melibiose, raffinose and soluble starch, negative in glycerol, D-arabinose, D-ribose, L-rhamnose, cellulose, inositol and D-mannitol, and marginal in lactose and salicin. Unlike a result on the above inorganic medium, raffinose is not utilized in Luedemann's organic medium. The activity of α-galactosidase is positive, and β-xylosidase and α-mannosidase negative. The physiological characteristics of strain M956-1 are shown in Table 2.

TABLE 2

Physiological characteristics of Strain M956-1

| | | |
|---|---|---|
| Hydrolysis of | | |
| Gelatin | | + |
| Starch | | + |
| Milk coagulation | | − |
| Peptoniazation | | − |
| Production of | | |
| Nitrate reductase | | +,−* |
| Tyrosinase | | − |
| Tolerance to | | |
| Lysozyme, 0.01% | | + |
| NaCl, 1–3% | | + |
| 4% | | − |
| pH 5.5–10.5 | | + |
| Temperature | | |
| Growth range | | 18° C.–49° C. |
| Optimal growth | | 37° C.–44° C. |
| No growth | | 15° C. and 50° C. |
| Utilization of** | | |
| | PG | Ld |
| Glycerol | − | − |

TABLE 2-continued

| Physiological characteristics of Strain M956-1 | | |
|---|---|---|
| D-Arabinose | − | − |
| L-Arabinose | + | + |
| D-Xylose | + | + |
| D-Ribose | − | ± |
| L-Rhamnose | − | − |
| D-Glucose | + | + |
| D-Galactose | + | + |
| D-Fructose | ± | + |
| D-Mannose | + | + |
| L-Sorbose | − | − |
| Sucrose | + | + |
| Lactose | ± | ± |
| Cellobiose | + | + |
| Melibiose | + | + |
| Trehalose | ± | + |
| Raffinose | + | − |
| D-Melezitose | − | − |
| Soluble starch | + | + |
| Cellulose | − | − |
| Dulcitol | − | − |
| Inositol | − | − |
| D-Mannitol | − | − |
| D-Sorbitol | − | − |
| Salicin | ± | ± |
| Activity of | | |
| α-Glucosidase | + | |
| β-Glucosidase | + | |
| α-Galactosidase | + | |
| β-Galactosidase | + | |
| β-Xylosidase | − | |
| α-Mannosidase | − | |

*Positive in Czapek's sucrose-nitrate broth, and negative in peptone-nitrate broth
**Basal media: PG; Pridham-Gottlieb' inorganic medium (ISP Medium No. 9), and Ld; Luedemann's yeast extract-CaCO₃ medium

Cell Chemistry

Purified cell wall of strain M956-1 contains mesodiaminopimelic acid and glycine but not 3-hydroxydiaminopimelic acid. The whole cell hydrolysate and purified cell wall contain easily detectable amounts of glucose and mannose, and traces of xylose and arabinose. Therefore, the strain belongs to Type II cell wall and Pattern D whole cell sugar.

The phospholipids present are phosphatidyl-glycerol, phosphatidyl-inositol and phosphatidyl-ethanolamines, and hence the type is P-II. Mass spectra show that the major menaquinones are MK-g (H4) and MK-10 (H4). Glycolate test is positive; hence the strain has glycolyl-muramic acid in the peptidoglycan.

Taxonomic Position

According to the descriptions of Luedemann[1] and Kawamoto, et al.,[2];[3], the following characteristics of strain M-956-1 are diagnostic for the systematics of

*Micromonospora:*

(1) spore with blunt short spines, (2) meso-diaminopimelic acid without 3-hydroxy isomer in cell wall, (3) large amounts of glucose and mannose and trace amounts of xylose and arabinose in cell wall, (4) colorless, pale yellow to light yellowish orange vegetative mycelium but none of diagnostic pigments, and (5) sugar utilization, positive in melibiose and raffinose, but negative in D-mannitol, L-rhamnose, D-arabinose and D-ribose, (6) activity of glycosidase, positive in α-galactosidase, and negative in β-xylosidase and α-mannosidase.

(1) Luedemann, G. M. Genus *Micromonospora* orskov 1923, p. 846–855. In R. E. Buchanan and N. E. Gibbons (ed.), Bergey's Manual of Determinative Bacteriology 8th Ed. Ed 1974. The Williams and Wilkins Company, Balt.
(2) Kawamoto, I., T. Oka and T. Nara: cell wall composition of *Micromonospora olivasterospora, Micromonospora sagamiensis* and related organisms. J. Bacteriol. 146: 527–534, 1981.
(3) Kawamoto, I., T. Oka and T. Nara: Carbon and nitrogen utilization by *Micromonospora* strains. Agric. Biol. Chem. 47: 203–215, 1983.

Differential characteristics of Strain M956-1 from 23 species of *Micromonospora* are shown in Table 3. In addition to the blackening after sporulation, most species of *Micromonospora* are characterized by intra- or extra-cellular distinct pigmentations which consist of diverse chromogenic compounds on each strain. However, Strain M956-1, *M. globosa, M. inositola, M. aurantiaca* and *M. echinospora* subsp. *pallida* form only light yellowish orange vegetative mycelia, and hence are non-chromogenic type. As shown in Table 4, the above four species had significant differences from Strain M956-1.

Both *M. chalcea* and Strain M956-1 have common characteristics consisting of the monopodial sporophore in cluster, the lack of diagnostic pigment, the formation of fluorescent yellow pigment, the profile of sugar utilization and the cell wall composition. *M. chalcea* may be differentiated from the present producing strain in spores with much smaller spines, the formation of reddish orange to reddish brown vegetative mycelia, the utilization raffinose in Luedemann's medium, the decomposition of cellulose and the inability to grow at 45° C.

Thus, Strain M956-1 is considered to be classified as a new species of *Micromonospora*. and is proposed to be designated *Micromonospora chersina* sp. nov. (chersina, Gr. f. adj. *khersinos:* "living in dry land" referring to the savanna vegetation where this organism lived in.)

TABLE 3

| Differential characteristics of Strain M956-1 and twenty-three species of Micromonospora | | | | | | | | |
|---|---|---|---|---|---|---|---|---|
| | Spine on | Cell wall*1 | | | | Major*2 | Utilization of *3 | | |
| | Spore | DAP isomer | Xyl. | Arab. | Glu. | menaquinone | Mel. | Raf. | Mtl. |
| Strain M956-1 | + | Meso | + | + | ++++ | MK9(H4), MK10(H4) | + | + | − |
| M. globosa | − | Meso | + | + | ++++ | MK10(H4) | + | + | − |
| M. fusca, M. chalcea and M. melanosporea | − | Meso | ++++ | ++ | +~++++ | MK10(H4)/ND | + | + | − |
| M. carbonacea and other 4 species*4 | − | Meso and 3-hydroxy | ++++ | ++++ | ++~++++ | MK9(H4)/MK10 (H4) | + | + | − |
| M. rosaria and M. inositola | − | Meso and | ++++ | +,++ | ++++,− | MK10(H4)/ND | + | −,+ | + |
| M. coerulea | − | Meso | ++++ | ++ | − | ND | + | + | + |
| M. narashinoensis and M. purpureochromogenes | − | Meso | ++++ | ++ | −,++ | MK10(H4,H6) | + | + | − |

TABLE 3-continued

| | Differential characteristics of Strain M956-1 and twenty-three species of Micromonospora | | | | | | | |
|---|---|---|---|---|---|---|---|---|
| | Spine on Spore | Cell wall*[1] | | | Major*[2] | Utilization of *[3] | | |
| | | DAP isomer | Xyl. | Arab. | Glu. | menaquinone | Mel. | Raf. | Mtl. |
| M. echinospora and other 8 species*[5] | + | 3-Hydroxy | ++++ | ++,++++ | −~++++ | MK10(H4)/MK 10(H6)/MK12(H4,6,8) | − | − | − |

*[1]DAP: diaminopimelic acid, Xyl.: xylose, Arab.: arabinose, Glu.: glucose
*[2]MK10(H4)/ND: one or two species have MK-10(H4) and another has no data. MK9(H4)/MK10(H4):MK-9(Hr) or MK-10(H4)
*[3]Mel.: melibiose, Raf.: raffinose, Mtl.: D-mannitol
*[4]M. megalomicea subsp. nigra, M. carbonacea subsp. aurantiaca, M. halophytica subsp. nigra and M. parva
*[5]M. echinospora subsp. ferruginea, M. echinospora subsp. pallida, M. purpurea, M. sagamiensis, M. grisea, M. olivasterospora, M. zionensis, and M. inyoenisis

TABLE 4

Differential characteristics of four Micromonospora species which are similar to Strain M956-1 in the growth color

| | Differences from Strain M956-1 |
|---|---|
| M. qlobosa | Rough spore surface. Major menaquinone: MK-10 (H4). Glycolate test-negative. Orange mycelial color in ISP No. 2 medium and nutrient agar. Utilization of lactose, β-xylosidase, positive. Inability to grow at 45° C. |
| M. inositola | Warty spore surface. Meso- and 3-hydroxy-diaminopimelic acid; a lot of xylose and absence of glucose in the cell wall. Orange mycelial color. Utilization of D-mannitol. Growth range: 25–40° C. β-xylosidase, positive. |
| M. aurantiaca | Lack of dark colors due to poor sporulation. Utilization of L-rhamnose and D-mannitol. Cellulose decomposition. Inability to grow at 45° C. |
| M. echinospora subsp. pallida | 3-Hydroxy-diaminopimelic acid and a large amount of xylose in the cell wall. Major menaquinone: MK-12. Different sugar utilization profile (negative: melibiose and raffinose, positive: L-rhamnose). Inability to grow at 45° C. |

It is to be understood that the present invention is not limited to use of the particular preferred strain M956-1 described above or to organisms fully answering the above descriptions. It is especially intended to include other BU-3420T-producing variant or mutant strains of the said organism which can be produced by conventional means such as x-radiation, ultraviolet radiation, treatment with nitrogen mustards, phage exposure, and the like.

Preparation of BU-3420T

BU-3420T is produced by cultivating a BU-3420T-producing strain of *Micromonospora chersina* , sp. nov., preferably a strain having the characteristics of *Micromonospora chersina* strain M956-1 (ATCC 53710) or a variant or mutant thereof, under submerged aerobic conditions in an aqueous nutrient medium. The producing organism is grown in a nutrient medium containing an assimilable carbon source, for example L-arabinose, D-xylose, sucrose, melibiose, raffinose or soluble starch. The nutrient medium should also contain an assimilable nitrogen source such as fish meal, peptone, soybean flour, peanut meal, cottonseed meal or corn steep liquor. Nutrient inorganic salts can also be incorporated in the medium. Such salts may comprise any of the usual salts capable of providing sodium, potassium, ammonium, calcium, phosphate, sulfate, chloride, bromide, nitrate, carbonate, or like ions.

Production of BU-3420T can be effected at any temperature conducive to satisfactory growth of the organism, e.g., 18° C. to 49° C., and is conveniently carried out at a temperature of about 28° C.

The fermentation may be carried out in flasks or in laboratory or industrial fermentors of various capacities. When tank fermentation is to be used, it is desirable to produce a vegetative inoculum in a nutrient broth by inoculating a small volume of the culture medium with a slant or soil culture or a lyophilized culture of the organism. After obtaining an active inoculum in this manner, it is transferred aseptically to the fermentation tank medium for large scale production of BU-3420T. The medium in which the vegetative inoculum is produced can be the same as, or different from, that utilized in the tank as long as it is such that a good growth of the producing organism is obtained.

In general, optimum production of BU-3420T is achieved after incubation periods of about 3–4 days. Antibiotic production may be monitored by the paper disc-agar diffusion assay using *Bacillus subtilis* (pH 8.0) as the test organism.

Isolation and Purification

BU-3420T may be isolated from the fermentation broth by conventional isolation and purification procedures, e.g., solvent extraction and chromatography. Example 5 below illustrates a preferred isolation and purification procedure for obtaining BU-3420T in substantially pure form.

Example 3 illustrates preparation of the triacetyl derivative of BU-3420T. This derivative may be obtained by reacting BU-3420T with an acetylating agent such as acetic anhydride in an inert organic solvent.

Physiochemical Properties of BU-3420T and BU-3420T Triacetate

BU-3420T was obtained as a blue amorphous solid, while its triacetate appeared as orange needles. BU-3420T is soluble in dimethyl sulfoxide, dimethylformamide and dioxane, slightly soluble in chloroform, ethyl acetate, methanol and ethanol, and insoluble in water and n-hexane. The acetate shows much improved solubility in organic solvents such as chloroform, methanol and ethanol. The molecular formula of BU-3420T and the acetate were established as $C_{30}H_{19}NO_9$ and $C_{36}H_{25}NO_{12}$, respectively, based on microanalysis, mass spectrum and $^{13}C$-NMR data of the acetate, and comparative spectral analysis of BU-3420T and the acetate. The physico-chemical data of both compounds are summarized in Table 5. The IR spectrum of BU-3420T (FIG. 1) has absorption bands at 3420, 3350, 2930, 1660, 1630, 1587, 1480, 1385, 1300, 1280, 1180 and 785 $cm^{-1}$. The carbonyl absorption at 1630 $cm^-$ suggests a quinone group in the molecule. The IR spectrum of the acetate exhibits a strong carbonyl absorption at 1770 $cm^{-1}$ in addition to the absorption bands of BU-3420T, indicating the production of enol (phenol) acetate. The $^1$H-NMR of BU-3420T acetate shows one methyl (δ:1.25 ppm), three acetyl methyl (2.34, 2.36 and 2.44 ppm), one OCH$_3$ (3.79 ppm), three methine (3.55, 4.78 and 5.04 ppm), two olefinic (6.05 and 6.07 ppm) and three aromatic protons (7.62×2 and 8.03 ppm). Two other protons at δ:9.41 and 12.37 ppm, are lost with D$_2$O addition. The spectrum of BU-3420T is similar to that of the acetate, but it lacks the three acetyl methyl signals observed for the latter. In the $^{13}$C-NMR, BU-3420T acetate showed 36 carbon signals including four methyl (δ18–21 ppm), three methine (31–43 ppm), one OCH$_3$ (57.7 ppm), six quarternary (63–99 ppm), sixteen sp$_2$ (114–153 ppm) and six carbonyl carbons (167–183 ppm).

Structure Determination

BU-3420T shows UV absorption maxima at 240, 287, 395 568 and 597 nm in a neutral solution. The absorption and its shift in alkaline solution resemble those of ε-rhodomycinonel,[1,2] Acetylation of BU-3420T afforded a tri-O-acetyl derivative which showed UV absorption at 244, 313 and 482 nm. Its IR spectrum indicated an enol-acetate and the $^1$H-NMR showed that three aromatic protons of BU-3420T (δ:7.32, 2H and 7.42 ppm) underwent down-field shift by the acetylation (7.62, 2H and 8.03 ppm). The presence of two quinone carbonyl carbons (180.6 and 182.7 ppm) was suggested by the $^{13}$C—NMR. Analyses of these spectral data illustrated

TABLE 5
Physico-chemical properties of BU-3420T

| | BU-3420T | BU-3420T Acetate |
|---|---|---|
| Nature | Blue amorphous powder | Orange rods |
| M.p. (dec) | 208–210° C. | 228–231° C. |
| $[\alpha]_D^{24}$ | +270° (c 0.01, DMF) | +1,300° (c 0.05, MeOH) |
| UVλ$_{max}$ nm (ε) | | |
| in MeOH | 240(8,300), 287(sh), 395(2,600), 568(4,200), 597(4,100) | 244(40,100), 313(6,700), 482(8,100) |
| in 0.01N HCl-MeOH | 239(8,300), 284(sh), 394(4,000), 563(3,600), 600(3,300) | 245(41,300), 317(6,700), 492(7,500) |
| in 0.01N NaOH-MeOH | 216(15,500), 246(23,000), 274(sh), 394(3,700), 597(10,200), 641(10,500) | 218(24,600), 246(26,200), 275(sh), 598(11,900), 640(11,900) |
| Molecular formula | C$_{30}$H$_{19}$NO$_9$ | C$_{36}$H$_{25}$NO$_{12}$ |
| Microanalysis | | Calcd for C$_{36}$H$_{25}$NO$_{12}$ · H$_2$O   Found |
| | | C % 63.43   63.20 |
| | | H % 3.99   3.75 |
| | | N % 2.06   2.16 |
| Secondary ion mass spectrum | M/z 538 (M + H)$^+$ | m/z 664 (M + H)$^+$ |
| TLC, SiO$_2$ (Xylene-Methyl ethyl ketone-Methanol = 5:5:1 v/v) | Rf 0.40 | 0.33 |

TABLE 6
$^1$H-NMR spectrum of BU-3420T-triacetate (400 MHz in DMSO-d$_6$)

| Proton | BU-3420T-triacetate |
|---|---|
| 4-CH$_3$ | 1.25(3H,d,J=7.3Hz) |
| 10, 12, & 15-OCOCH$_3$ | 2.33(3H,s), 2.36(3H,s), 2.44(3H,s) |
| 4-H | 3.55(1H,q,J=7.3Hz) |
| 6-OCH$_3$ | 3.79(3H,s) |
| 7-H | 4.78(1H,s) |
| 2-H | 5.04(1H,d,J=3.8Hz) |
| 19-H | 6.05(1H,d,J=1.3Hz) |
| 20-H | 6.07(1H,d,J=1.3Hz) |
| 13 & 14-H | 7.62(2H,s ×2) |
| 9-H | 8.03(1H,s) |
| 1-NH | *9.41(1H,d,J=3.8Hz) |
| 5-COOH | *12.37(1H,br) |

*disappear by D$_2$O addition the following 1,4,6-triacetoxy8,9-substituted anthraquinone structure (partial structure A) to the antibiotic acetate. Thus, the remaining part of the molecule should have one C—CH$_3$, one OCH$_3$, three —CH<, two —CH=, two >C=, six quarternary carbons and one carbonyl group based on the 1H— and $^{13}$C—NMR data. Among the six quarternary carbons, four carbons appeared at δ:88.8, 89.6, 97.3 and 99.4 ppm which strongly suggested a conjugated di-yne structure. Additional evidence on this moiety was provided by the $^1$H—$^{13}$C long range correlation experiment (COLOC) which showed the partial structure (B). This unusual functionality was recently discovered in esperamicin[1] and calichemicin[4], extraordinary potent antitumor antibiotics produced by an Actinomadura strain[5] and a Micromonospora strain[6], respectively. From the consideration of the various NMR experiments, the following partial structures were derived in addition to the above assigned structures (A and B).

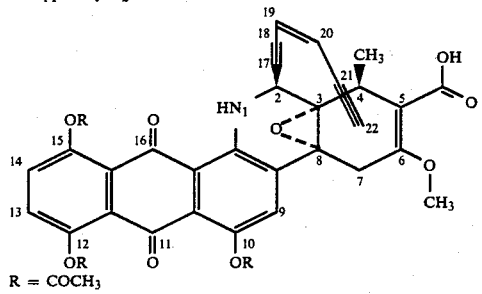

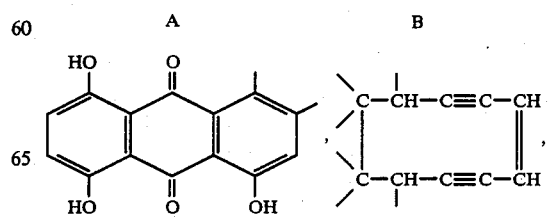

-continued

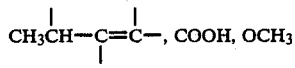

The complete structure of triacetyl-BU-3420T was elucidated by X-ray crystallography. Consequently, the structure of BU-3420T was determined as below. The assigned structure is in accord with the all spectral data obtained for the antibiotic and its triacetate (Table 6).

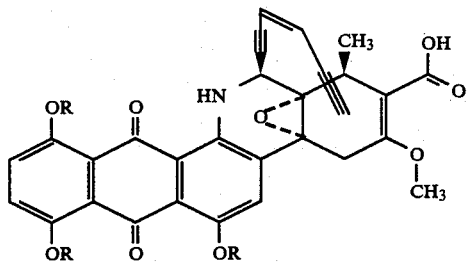

BU-3420T: R = H—

Triacetyl BU-3420T: R = CH₃CO—

(1) *J. Antibiotics* 33:1331–1340, 1980.
(2) *J. Antibiotics* 33:1341–1347, 1980.
(3) *J. Am. Chem. Soc.* 109:3462–3464, 1987.
(4) *J. Am. Chem. Soc.* 109:3466–3468, 1987.
(5) U.S. Pat. No. 4,675,187.
(6) Program and abstracts of 26th Interscience Conference on Antimicrobial Agents and Chemotherapy; September, 1986, Abstract 227.

Biological Activity of BU-3420T and its Triacetate Derivative

In vitro antibacterial and antifungal activities

The minimum inhibitory concentrations (MICs) of BU-3420T and its acetate were determined by a serial agar dilution method. Nutrient agar (Eiken) and GAM agar medium (Nissui) were used for aerobic and anaerobic bacteria, respectively. Table 7 shows in vitro antibacterial activity of BU-3420T and its acetate in comparison with kanamycin A and clindamycin. Against Gram-positive aerobic bacteria, BU-3420T and its acetate showed intensely potent activity, whereas Gram-negative organisms were a little less susceptible. Also, both compounds were much more active than clindamycin against anaerobic Gram-positive and negative bacteria. Certain kanamycin- and clindamycinresistant bacteria were susceptible to both compounds. On the whole. BU-3420T acetate was two to eight times more potent than BU-3420T against aerobic and anaerobic bacteria.

In vitro antifungal activity of BU-3420T and its acetate was also determined in Sabouraud dextrose agar. As shown in Table B, BU-3420T acetate was significantly more potent than amphotericin B against all of the organisms tested except for *Cryptococcus neoformans* which was more susceptible to amphotericin B. Similar to their antibacterial activity, BU-3420T acetate showed in vitro antifungal activity 4 to 64 times more potent than that of BU-3420T.

In vivo activity and acute toxicity

The in vivo efficacy of BU-3420T was assessed in the experimental infection of mice caused by *Staphylococcus aureus* Smith. Mice were challenged intraperitoneally with 100 times the lethal dose of the pathogen in a 5% suspension of hog gastric mucin (American Laboratory, Omaha, Neb.). BU-3420T was administered to mice intramuscularly just before the bacterial challenge. The mice were observed for 5 days to determine the median protective dose ($PD_{50}$). As shown in Table 9, BU-3420T exhibited favorable in vivo efficacy, and its $PD_{50}$ was found to be 0.13 mg/kg. BU-3420T did not show any toxicity after an intramuscular administration of 5 mg/kg to mice.

TABLE 7

| Antibacterial spectra of BU-3420T and its acetate | | | | |
|---|---|---|---|---|
| | MIC (mcg/ml) | | | |
| | BU-3420T | BU-3420T acetate | Kanamycin A | Clindamycin |
| Aerobic organism | | | | |
| *Staphylococcus aureus* 209P | 0.000013 | 0.0000063 | 0.2 | |
| *Staphylococcus aureus* Smith | 0.000025 | 0.0000063 | 0.8 | |
| *Staphylococcus aureus* A20234[a] | 0.000025 | 0.0000063 | 100 | |
| *Staphylococcus aureus* BX1633[b] | 0.000025 | 0.0000063 | 0.8 | |
| *Staphylococcus aureus* A15097[c] | 0.000025 | 0.0000063 | 0.8 | |
| *Staphylococcus epidermidis* D153 | 0.0000063 | 0.0000031 | 0.4 | |
| *Staphylococcus epidermidis* A22152[a] | 0.00005 | 0.000013 | 12.5 | |
| *Enterococcus faecalis* A9612 | 0.0004 | 0.0001 | 25 | |
| *Micrococcus luteus* 1001 | 0.0008 | 0.0002 | 3.1 | |
| *Bacillus subtilis* PCI-219 | 0.0000063 | 0.0000031 | 0.2 | |
| *Escherichia coli* NIHJ | 0.05 | 0.0063 | 1.6 | |
| *Escherichia coli* Juhl | 0.05 | 0.0063 | 6.3 | |
| *Escherichia coli* A20665[a] | 0.05 | 0.013 | >100 | |
| *Escherichia coli* A9624[a] | 0.05 | 0.0063 | >100 | |
| *Escherichia coli* A20341-1[b] | 0.2 | 0.025 | 6.3 | |
| *Enterobacter cloacae* A9659 | 0.05 | 0.0063 | 3.1 | |
| *Klebsiella pneumoniae* D11 | 0.0063 | 0.0008 | 0.4 | |
| *Klebsiella pneumoniae* A20680[a] | 0.1 | 0.013 | >100 | |
| *Pseudomonas aeruginosa* A9930 | 0.025 | 0.0063 | 25 | |
| *Proteus vulgaris* A9436 | 0.0063 | 0.0031 | 0.4 | |
| *Proteus mirabilis* A9554 | 0.013 | 0.0031 | 3.1 | |
| *Morganella morganii* A9553 | 0.0063 | 0.0031 | 3.1 | |
| *Serratia marcescens* A20222 | 0.1 | 0.0063 | 6.3 | |
| Anaerobic organism | | | | |
| *Clostridium difficile* A21675[d] | 0.0063 | 0.0031 | | >100 |
| *Clostridium perfringens* A9635 | 0.025 | 0.013 | | 0.025 |
| *Propionibacterium acnes* A21933 | 0.013 | 0.013 | | 0.4 |

TABLE 7-continued

| Antibacterial spectra of BU-3420T and its acetate | | | | |
|---|---|---|---|---|
| | MIC (mcg/ml) | | | |
| | BU-3420T | BU-3420T acetate | Kanamycin A | Clindamycin |
| *Peptostreptococcus anaerobius* A21905 | 0.1 | 0.025 | | 0.4 |
| *Bacteroides fragilis* A22693 | 0.2 | 0.1 | | 0.05 |
| *Bacteroides fragilis* A22534[b] | 0.1 | 0.05 | | 0.8 |

[a]Kanamycin-resistant
[b]Ampicillin-resistant
[c]Methicillin-resistant
[d]Clindamycin-resistant

TABLE 8

| Antifungal activity of BU-3420T and its acetate | | | |
|---|---|---|---|
| | MIC (mcg/ml) | | |
| Test organism | BU-3420T | BU-3420T acetate | Amphotericin B |
| *Candida albicans* IAM4888 | 12.5 | 0.4 | 1.6 |
| *Candida albicans* A9540 | 6.3 | 0.2 | 1.6 |
| *Cryptococcus neoformans* D49 | 12.5 | 0.8 | <0.2 |
| *Cryptococcus neoformans* IAM4514 | 12.5 | 0.8 | <0.2 |
| *Aspergillus fumigatus* IAM2530 | 6.3 | 0.1 | 1.6 |
| *Aspergillus fumigatus* IAM2034 | 3.1 | <0.05 | 1.6 |
| *Aspergillus flavus* FA21436 | 25 | 0.4 | 3.1 |
| *Fusarium moniliforme* A2284 | 0.1 | <0.05 | 12.5 |
| *Piricularia oryzae* D91 | 12.5 | 0.4 | 3.1 |
| *Trichophyton mentagrophytes* D155 | 12.5 | 0.4 | 6.3 |
| *Trichophyton mentagrophytes* #4329 | 12.5 | 0.8 | 3.1 |
| *Sporothrix shenckii* IFO8159 | 25 | 3.1 | 50 |
| *Petriellidium boydii* IFO8073 | 6.3 | 0.1 | >100 |
| *Mucor spinosus* IFO5317 | 12.5 | 0.2 | 0.8 |

TABLE 9

| In vivo activity of BU-3420T against *S. aureus* Smith infection (ip) in mice Treatment: single, im | |
|---|---|
| Dose (mg/kg, im) | No. of survivor/tested |
| 2.5 | 5/5 |
| 0.63 | 5/5 |
| 0.16 | 3/5 |
| 0.04 | 0/5 |
| 0.01 | 0/5 |
| $PD_{50}$: | 0.13 mg/kg, im |

Antitumor Activity of BU-3420T

BU-3420T and its acetate derivative were tested for in vitro cytotoxicity against several murine and human tumor cell lines and for in vivo antitumor activity in tumor-bearing mice. Mitomycin C was used as a reference compound in both in vitro and in vivo experiments. B16-F10 (murine melanoma), P388 (murine Leukemia), P388/VCR (vincristine-resistant P388) and Moser (human colorectal carcinoma) cells were grown to the logarithmic phase in the enriched Eagle minimum essential medium (MEM) supplemented with fetal calf serum (FCS, 10%) and kanamycin (60 mcg/ml), and HCT-116 (human colon carcinoma) cells in Maccoy's 5A medium supplemented with FCS (10%), penicillin (100 μ/ml) and streptomycin (100 mcg/ml), and were harvested and inoculated into wells of the 96-or 24-well tissue culture plate with test materials at the concentration of $1.5 \times 10^5$, $1.2 \times 10^4$, $1.2 \times 10^4$, $2.5 \times 10^5$ and $3.0 \times 10^5$ cells/ml, respectively. They were incubated at 37° C. in a humidified atmosphere of 5% $CO_2$ and 95% air for 72 hours. The cytotoxic activities against B16-F10, Moser and HCT-116 cells were determined colorimetrically at 540 nm after staining viable cells with 0.006% neutral red solution. On the other hand, the cytotoxic activities against P388 and P388/VCR cells were determined by counting the number of viable cells. The results are summarized in Table 10. BU-3420T exhibited potent cytotoxicity against both murine and human tumor cell lines tested. Although human tumor cell lines, Moser and HCT-116 cells seemed to be slightly more resistant to mitomycin C than murine tumor cell line, B16-F10, they were conversely 6 to 12 times more sensitive to BU-3420T. Furthermore, BU-3420T showed the same cytotoxicities against both VCR-sensitive and resistant P388 cells. The cytotoxicity of the acetate derivative of BU-3420T was more potent than that of the parent compound, especially against Moser cells.

Inhibitory effects of BU-3420T on macromolecule (DNA, RNA and protein) synthesis were determined in vitro. Cultured L1210 cells ($5 \times 10^5$ cells/ml) were preincubated with BU-3420T at 37° C. for 15 min. Isotopically labelled precursor, $^3$H-thymidine, $^{14}$C-uridine or $^3$H-leucine was added into the cultured mixture and further incubated for 60 min. After washing with chilled 5% trichloroacetic acid, the radioactivity incorporated into the acid-insoluble fraction of the tumor cells was determined in a liquid scintillation counter. As shown in Table 11, BU-3420T inhibited DNA synthesis approximately 500 and 100 times more than RNA and protein synthesis, respectively.

In vivo antitumor activities of BU-3420T and its acetate derivative were determined in tumor-bearing $CDF_1$ or $BDF_1$ mice. Female $CDF_1$ mice were intraperitoneally inoculated with 0.5 ml of 10% melanotic melanoma B16 brei. Test compounds were administered to the mice intraperitoneally by the following treatment schedules; once a day on days 1, 2 and 3 (QD×3), on days 1, 5 and 9 (Q4D×3) and on days 1 to 9 (QD×9). As shown in Table 12, both BU-3420T and its acetate derivative gave good anti-P388 potencies with activity at broad dose ranges even though their T/C values were maintained at low levels, maximum T/C values being 135%. They were at least 10 times more potent than mitomycin C in terms of minimum effective dose. In the B16 system, both compounds gave approximately similar results to those in the P388 system (Table 13).

TABLE 10

In vitro cytotoxicities against murine and human tumor cells

| Compound | IC50 (mcg/ml) | | | | |
|---|---|---|---|---|---|
| | B16-F10 | P388 | P388/VCR | Moser | HCT-116 |
| BU-3420T | 0.0052 | 0.0004 | 0.0004 | 0.00085 | 0.00042 |
| BU-3420T-acetate | 0.0007 | ND* | ND* | 0.000003 | ND* |
| Mitomycin C | 0.5 | ND* | ND* | 1.2 | 0.8 |

*ND: Not done

TABLE 11

Inhibition of macromolecule synthesis in L1210 leukemia

| Compound | IC50 (mcg/ml) | | |
|---|---|---|---|
| | DNA | RNA | Protein |
| BU-3420T | 0.018 | 9.2 | 1.5 |
| Mitomycin C | 1.7 | >100 | >100 |

TABLE 12

Antitumor activity against P388 leukemia (ip)

| Compound | Dose*1 (mg/kg/day) | MST*2 (day) | T/C (%) | Body weight change on day 4 (g) |
|---|---|---|---|---|
| BU-3420T | 1.0 | 13.5 | 135*3 | −0.5 |
| | 0.5 | 13.0 | 130*3 | 0.0 |
| | 0.25 | 13.5 | 135*3 | +0.8 |
| | 0.13 | 13.0 | 130*3 | +0.8 |
| | 0.063 | 13.0 | 130*3 | +0.3 |
| | 0.031 | 13.0 | 130*3 | +1.0 |
| BU-3420T-acetate | 1.0 | 11.0 | 110 | −0.8 |
| | 0.5 | 13.5 | 135*3 | −0.5 |
| | 0.25 | 13.5 | 135*3 | −1.0 |
| | 0.13 | 12.5 | 125*3 | 0.0 |
| | 0.063 | 12.5 | 125*3 | +0.5 |
| | 0.031 | 13.0 | 130*3 | +1.5 |
| Mitomycin C | 3.0 | 20.0 | 200*3 | −1.0 |
| | 1.0 | 13.5 | 135*3 | +0.5 |
| | 0.3 | 14.0 | 140*3 | +1.0 |
| | 0.1 | 11.5 | 115 | +1.8 |
| Vehicle | — | 10.0 | — | +2.4 |

*1QD × 3, ip
*2Median survival time
*3Significant antitumor effect (T/C ≧ 125%)

TABLE 13

Antitumor activity against B16 melanoma (ip)

| Compound | Dose*1 (mg/kg/day) | MST*2 (day) | T/C (%) | Body weight change on day 5 (g) |
|---|---|---|---|---|
| BU-3420T | 1.0 | 21.5 | 159*3 | −0.5 |
| | 0.5 | 18.5 | 137*3 | −0.5 |
| | 0.25 | 18.5 | 137*3 | +0.8 |
| | 0.13 | 16.5 | 122 | +0.8 |
| | 0.063 | 19.0 | 141*3 | +0.8 |
| | 0.031 | 16.5 | 122 | +1.0 |
| BU-3420T-acetate | 1.0 | 16.5 | 122 | −0.3 |
| | 0.5 | 21.0 | 156*3 | +0.5 |
| | 0.25 | 18.5 | 137*3 | +0.5 |
| | 0.13 | 21.0 | 156*3 | +0.3 |
| | 0.063 | 15.5 | 115 | +1.0 |
| | 0.031 | 16.0 | 119 | −0.3 |
| Mitomycin C | 2.0 | 30.0 | 222*3 | +0.5 |
| | 1.0 | 20.5 | 152*3 | +1.0 |
| | 0.5 | 18.0 | 133*3 | 0.0 |
| | 0.25 | 15.0 | 111 | +0.8 |
| Vehicle | — | 13.5 | — | +1.0 |

*1QD × 9, ip for BU-3420T and Q4D × 3, ip for BU-3420T-acetate and mitomycin C
*2Median survival time
*3Significant antitumor effect (T/C ≧ 125%)

As shown above BU-3420T and its triacetyl derivative possess potent antibacterial and antifungal activity and are thus useful in the therapeutic treatment of mammals and other animals for diseases caused by such organisms. Additionally the compounds may be utilized for other conventional applications of antimicrobial agents such as disinfecting medical and dental equipment.

The in vitro and in vivo antitumor data presented above indicate that BU-3420T and its triacetyl derivative are also therapeutically useful in inhibiting the growth of malignant tumors in mammalian hosts.

The present invention, therefore, provides a method for therapeutically treating an animal host affected by a bacterial or fungal infection which comprises administering to said host an effective antibacterial or antifungal dose of BU-3420T or BU-3420T triacetate, or a pharmaceutical composition thereof.

Also provided is a method for inhibiting the growth of malignant tumors in mammals which comprises administering to said mammalian host an effective tumor-inhibiting dose of BU-3420T or BU-3420T triacetate, or a pharmaceutical composition thereof.

In another aspect the present invention provides a pharmaceutical composition which comprises an effective antibacterial or antifungal amount of BU-3420T or BU-3420T triacetate in combination with an inert pharmaceutically acceptable carrier or diluent.

Additionally, the invention provides a pharmaceutical composition which comprises an effective tumor-inhibiting amount of BU-3420T or BU-3420T triacetate in combination with an inert pharmaceutically acceptable carrier or diluent.

The pharmaceutical compositions may contain other active antimicrobial or antitumor agents and may be made up in any pharmaceutical form appropriate for the desired route of administration. Examples of such compositions include solid compositions for oral administration such as tablets, capsules, pills, powders and granules, liquid compositions for oral administration such as solutions, suspensions, syrups or elixers and preparation for parenteral administration such as sterile solutions, suspensions or emulsions. They may also be manufactured in the form of sterile solid compositions which can be dissolved in sterile water, physiological saline or some other suitable sterile injectable medium immediately before use.

For use as an antimicrobial agent, the BU-3420T or BU-3420T triacetate, or pharmaceutical composition thereof, is administered so that the concentration of active ingredient is greater than the minimum inhibitory concentration for the particular organism being treated.

For use as an antitumor agent, optimal dosages and regimens of BU-3420T and BU-3420T triacetate for a given mammalian host can be readily ascertained by those skilled in the art. It will, of course, be appreciated that the actual dose of compound used will vary according to the particular composition formulated, the mode of application and the particular situs, host and disease being treated. Many factors that modify the action of the drug will be taken into account including age, weight, sex, diet, time of administration, route of administration, rate of excretion, condition of the patient, drug combinations, reaction sensitivities and severity of the disease.

The following examples are provided for illustrative purposes only and are not intended to limit the scope of the invention.

EXAMPLE 1

Fermentation of BU-3420T

A well grown agar slant of *Micromonospora* species, Strain No. M956-1, was used to inoculate five 500 ml Erlenmeyer flasks containing seed medium consisting of 1% lactose, 3% soluble starch (Nichiden Kagaku), 1% fish meal (Hokuyo Suisan), 0.6% $CaSO_4.2H_2O$ and 0.5% $CaCO_3$, the pH being adjusted to 7.0 before sterilization. The flasks were shaken at 32° C. for 7 days on a rotary shaker (200 rpm) and a 500-ml aliquot of the culture from the flasks was inoculated into a 20-liter stir-jar fermentor containing 12 liters of the second seed medium composed of 1.5% soluble starch, 0.5% glucose, 1% beet molasses (Nihon Tensai Seito), 1% fish meal and 0.5% $CaCO_3$ (pH 7.0). The fermentation was carried out at 28° C. for 92 hours with agitation at 250 rpm and aeration of 12 liters per minute. Two liters of the second seed was transferred into a 200-liter tank fermentor containing 120 liters of production medium having the same composition as the second seed medium described above. Fermentation was carried out at 28C. for 73 hours under agitation at 250 rpm and aeration rate of 120 liters per minute. The antibiotic production in the fermentation broth was extracted with n-BuOH and monitored by the paper-disc agar diffusion method using *Bacillus subtilis* (pH 8.0) as the test organism. The antibiotic production was extremely low, the maximum potency was less than 1 $\mu g/ml$.

Example 2

Isolation and Purification of BU-3420T

The harvested broth (220 liters) obtained according to Example 1 was adjusted to pH 2.0 with 6N HCl, n-butanol (λliters) was added and the reaction mixture was stirred for two hours. The mixture was separated to the organic and the aqueous layers with the aid of a Sharpless centrifuge (Kokusan, No. 4A). The organic extract (68 liters) was concentrated azeotropically by occasional addition of water in vacuo to an aqueous concentrate (one liter). The precipitate which deposited was collected by decantation, dissolved in methanol (2 liters) and combined with the aqueous filtrate. The combined solution was charged on a column of Diaion HP-20 (Mitsubishi Kasei, $\phi 10 \times 65$ cm) pretreated with 70% aqueous methanol. After being washed with 80% aqueous methanol, the activity was eluted with 80% aqueous acetone. The eluate was collected in 120 ml-fractions which were examined by paper disc assay using *Bacillus subtilis* PCI 219 as the test strain. The active fractions were pooled and evaporated in vacuo to afford a dark brown oily residue (62g). The residue was chromatographed on a column of Sephadex LH-20 ($\phi 4 \times 40$ cm) using methanol as the developing solvent. Upon monitoring the eluate by the bioassay (*B. subtilis* PCI 219) and TLC ($SiO_2$, xylene-methyl ethyl ketone-methanol=5:5:1 v/v, $R_f$ 0.40), the appropriate active fractions were concentrated in vacuo to afford 56 mg of a dark blue solid. This solid was further purified by preparative TLC using $SiO_2$ plates (Kieselgel 60 $F_{254}$, Merck) and xylene methyl ethyl ketone-methanol (5:5:1, v/v) as the developing solvent system. The blue band at around Rf 0.40 was scratched off and extracted with dioxane. Concentration of the extract yielded a homogeneous blue sample of BU-3420T (5.7 mg).

EXAMPLE 3

Triacetyl BU-3420T

BU-3420T (15 mg) was dissolved in acetic anhydride (1.5 ml) and pyridine (2ml) and the mixture was allowed to stand at room temperature for 18 hours. The resulting solution was mixed with 10 ml of ethyl acetate and washed with water (10 ml). After evaporation of the ethyl acetate layer, the residue was purified by preparative TLC ($SiO_2$ plate, xylene-methyl ethyl ketone-methanol=5:5:1 v/v Rf 0.33). The appropriate zone was extracted with ethyl acetate and the extract concentrated in vacuo. Crystallization of the residue from aqueous acetonitrile yielded orange needles of homogenous BU-3420T triacetate.

EXAMPLE 4

Preferred Fermentation Procedure A. Shake flask fermentation

*Micromonospora chersina* (strain M956-1, ATCC 53710) was maintained and transferred in test tubes on agar slants of yeast-malt extract agar. This medium consists of malt extract (1.0%), yeast extract (0.4%), dextrose (0.4%), agar (1.5%) and calcium carbonate (0.15%) in distilled water. With each transfer the agar slant was incubated for two weeks at 2B° C. To prepare an inoculum for the production phase, the surface growth from the slant culture was transferred to a 500 ml Erlenmeyer flask containing 100 ml of sterile medium consisting of lactose (1.0%), dextrin (3.0%), fishmeal (1.0%), calcium carbonate (0.5%), copper sulphate (0.6%) and sodium iodide (1 mg/l) in distilled water. This vegetative culture was incubated at 28° C. for 7 days on a rotary shaker set at 250 rpm. Five mls of this vegetative culture (8% sediment, pH 7.5) were transferred to a 500 ml Erlenmeyer flask containing 100 mls of a production medium consisting of starch (1.5%), glucose (0.5%), beet molasses (1.0%), fishmeal (1.0%), calcium carbonate (0.5%), copper sulphate (0.005%) and sodium iodide (5 mg/l) in distilled water. The production medium was incubated for four to six days on a rotary shaker set at an agitation rate of 250 rpm. Antibiotic production reached 4.5–5.0 $\mu g/ml$ at 120–144 hours, according to HPLC analysis.

B. Tank fermentation

Five mls of frozen vegetative culture of strain M956-1 (ATCC 53710) were used to inoculate a 500 ml Erlenmeyer flask containing 100 ml of a vegetative medium (VM-1) consisting of lactose (1%), dextrin (3.0%), fishmeal (1.0%), calcium carbonate (0.5%) and calcium sulphate (0.6%). The vegetative medium was incubated for five days at 2B° C on a rotary shaker set at an agitation rate of 250 rpm. Twenty-five mls of this vegetative (10% sediment, pH 7.1) were transferred to a 2 liters Vitro bottle containing 500 mls of a vegetative medium (VM-2) consisting of starch (1.5%), glucose (0.5%), beet molasses (1%), fishmeal (1%), and calcium carbonate (0.5%) in distilled water. This vegetative medium was incubated again at 28° C for 96 hours on a rotary shaker set at an agitation rate of 250 rpm. The resulting culture (12% sediment, pH 7.4) was crossed aseptically into a New Brunswick Microgen fermentor containing 10 liters of the production medium consisting of starch (1.0%), Pharmamedia (0.5%), calcium carbonate (0.1%), copper sulphate (0.005%) and sodium iodide (0.5 mg/l) in distilled water. The organism was allowed to grow under the following conditions: agitation rate set at 250 rpm, temperature set at 30° C and aeration set at 10 liters/ minute. Antibiotic production reached a maximum of 2.8μg/ml after 96 to 110 hours, according to HPLC analysis.

In another example, five mls of a frozen vegetative culture of strain M956-1 (ATCC 53710) were inoculated into an Erlenmeyer flask containing 100 mls of vegetative medium VM-1. This vegetative medium was incubated at 28° C. for five days on a rotary shaker set at an agitation rate of 250 rpm. Seventy mls of this vegetative (10% sediment, pH 7.1) were transferred to a Vitro bottle containing 1400 mls of the vegetative medium VM-2 and incubated at 28° C. for 96 hours on a rotary shaker set at an agitation rate of 250 rpm. The resulting vegetative medium was transferred aseptically into a 50 liter nominal volume Biolofitte fermentor containing 30 liters of production medium consisting of starch (1.5%), glucose (0.5%), beet molasses (1.0%), fishmeal (1.0%), calcium carbonate (0.5%) and sodium iodide (5 ml/l) in distilled water. An antifoam agent was used to control foaming. The organism was allowed to grow under the following fermentation conditions: agitation was set at a rate of 250 rpm, temperature was set at 30° C. and aeration at a rate of 35 liters/minute. Antibiotic production reached a peak of 2.4 μg/ml at 120–144 hours according to HPLC analysis.

EXAMPLE 5

Preferred Isolation and Purification Procedure

A highly simplified process was developed for the efficient purification of BU-3420T from the ferminitation broth. This process may be illustrated by the following scheme.

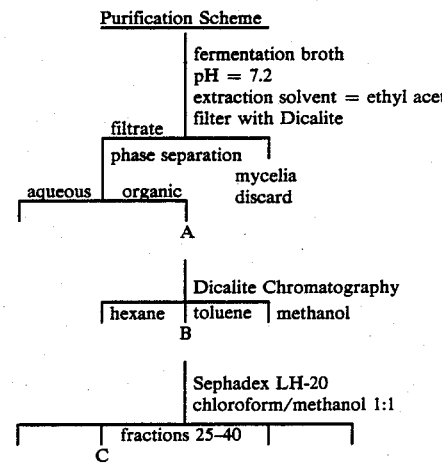

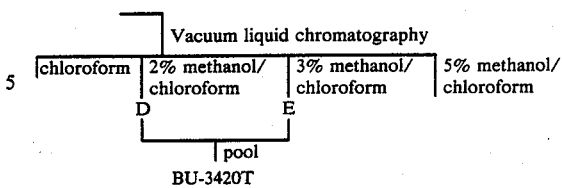

Methods and Materials

All solvents were of reagent grade and were used without further purification. Ethyl acetate, hexane, toluene, methanol, and chloroform were Fisher Scientific Company ACS grade solvents. Tetrahydrofuran was preservative free high purity solvent manufactured by American Burdick and Jackson Laboratories, Inc. Water refers to in house deionized water passed through a Barnstead Nanopure II D3700 Series cartridge deionization system (producing ASTM, CAP, NCCIS Type I Reagent Grade Water). Ammonium acetate was ACS HPLC grade reagent from Fisher Scientific Company. Dicalite was diatonaceous earth manufactured by Grefco, Inc., Torrance, Calif.

Thin Layer Chromatoqraphy (TLC):

TLC was carried out on Analtech precoated silica gel GHLF plates (2.5 cm×10 cm, 0.25 mm thick layer). The plates were developed in glass cylinders (6.4 cm [o.d]×11.5 cm high) purchased from Whatman, Inc. The tanks were lined with filter paper (Whatman %4), charged with 10 ml of of 1 part methanol, 9 parts chloroform, and allowed to equilibrate prior to introducing the plate. The developed, air-dried plates were viewed in visible light without any spray reagents.

Analytical HPLC

An analytical HPLC system was constructed from the following components: Waters Associates Model 6000A Solvent Delivery System pump a Hewlett Packard 1040A HPLC Detector System consisting of a HPB85B computer, a HP9121 Disc Drive, a 7470A Plotter and a 2225A Think Jet Printer; Water Associates Model U6K injector; Q-BEX #10015 ODS (10 μ) column (4.6 mm i.d.]×30 cm). The components were connected with 316 stainless steel tubing (1.6 mm [o.d.]- 0.23 mm [i.d.]). The eluant consisting of 55 parts 0.1M ammonium acetate, 45 parts tetrahydrofuran, was pumped at a flow rate of 2 ml/min. for all analysis.

Preparation of Crude Extract A

Raw fermentation broth (35L) at pH 7.2, as prepared according to the general procedure of Example 4, was mixed with an equal volume of ethyl acetate (35L) in a polypropylene tank and stirred for 2 hours using an air-driven mixer. Four large scoops of Dicalite (approximately 2 Kg) were mixed into the suspension. The resulting mixture was filtered using a centerslung basket centrifuge. The filtrate was allowed to develop two immiscible phases which were subsequently separated. The organic, ethyl acetate layer was concentrated in vacuo in a rotatory evaporator to yield 84.2 g of a dark greenish blue residue A.

Dicalite Chromatography of Residue A

A slurry of residue A (84.2 g), chloroform (200 ml), and Dicalite (100 g) was prepared in a 500 ml round bottom flask. After thorough mixing, the slurry was evaporated to dryness in vacuo in a rotatory evaporator. The resulting residue was dry-packed into a flash chromatography column (4.1 cm [i.d.]×46 cm). Elution commenced with pressurized flow (nitrogen, 3 psi) using the following elutropic series; 3 liters of hexane, 1 liter of toluene, and 1 liter of methanol. The toluene eluant was concentrated to dryness in vacuo in a rotatory evaporator to give 214.2 mg of residue B.

Sephadex LH-20 Chromatoqraphy of Residue B

A Spectrum Liquid Chromatography column (2.5 cm [i.d.]×70 cm) was packed with 80 g of Sephadex LH-20 gel (Pharmacia Fine chemicals, N.J.) which had been previously swollen in 500 ml of chloroform/methanol (1:1, v:v) for 24 hours. After overnight equilibration with 3 bed volumes of eluant, residue B in 10 ml of chloroform/methanol (1:1, v:v) was applied to the top of the column, and elution commenced with the mobile phase at a flow rate of 1.5 ml/min. After an initial 260 ml forerun, eighty-seven 10 ml fractions were collected. Aliquots (2–3 $\mu$l) from each fraction were analyze by TLC. Fractions 25–40 were pooled and concentrated in vacuo to yield 7.3 mg of residue C.

Vacuum Liquid Chromatography of Residue C

A sintered-glass Buchner filter funnel with a fritted disk (Kontes Scientific Glassware K-954100 Buchner funnel, medium [M]pore size 10–15 microns, 15 ml capacity) was dry packed to a height of 4 cm with TLC grade silica gel (Silica Gel 60, cat #7730, E. Merck, Darmstadt, Germany). The adsorbent was allowed to settle by gentle tapping under gravity followed by the application of vacuum to give a uniform and tightly packed hard cake. Vacuum was released and chloroform (30 ml) was applied to the surface of the adsorbent. The vacuum was again applied and the column sucked dry.

Residue C (7.3 mg) was preadsorbed on a small amount of the silica gel and uniformly applied to the top of the column. Elution commenced under gentle vacuum with the following elutropic series; chloroform (500 ml), 2% methanol in chloroform (200 ml), 3% methanol in chloroform (200 ml) and 5% methanol in chloroform (200 ml). The 2% methanol in chloroform and 3% methanol in chloroform fractions, were shown by TLC analysis, to contain exclusively a purple spot at $R_f$ 0.35. These were pooled and concentrated in vacuo to yield 1.3 mg of BU-3420T.

Physical and Chemical Properties of BU-3420T

The isolated BU-3420T has the following physical and spectral properties:

| Description: | Purple amorphous solid |
|---|---|
| Analytical Thin Layer Chromatography: | |
| Solvent System | $R_f$ value |
| $CHCl_3$/MeOH (9:1) | 0.35 |
| $CHCl_3$/MeOH (5:1) | 0.54 |
| Xylene/Methyl ethyl ketone/MeOH (5:5:1) | 0.53 |
| Ultraviolet Spectrum: | Reference No. 8727115 Hewlett Packard 8452A Diode Array Spectrophotometer Concentration: $1.25 \times 10^{-3}$ g/100 ml Solvent: Methanol |

| | max | $(E_{1\ cm}^{1\%})$ |
|---|---|---|
| Neutral | 597 nm | 112 |
| | 568 nm | 118 |
| | 395 nm | 64 |
| | 285 nm | sh |
| | 238 nm | 342 |

| Analytical HPLC: | |
|---|---|
| Mobile Phase | Retention Time |
| 55% 0.1% $NH_4OAc$/ 45% THF | 5.4 min |

What is claimed is:

1. A method for therapeutically treating an animal host affected by a fungal infection, which comprises administering to said host an effective antifungal dose of BU-3420T.

2. A method for therapeutically treating an animal host affected by a fungal infection, which comprises administering to said host an effective antifungal dose of BU-3420T triacetate.

* * * * *

UNITED STATES PATENT AND TRADEMARK OFFICE
CERTIFICATE OF CORRECTION

PATENT NO. : 4,952,572
DATED : August 28, 1990
INVENTOR(S) : H. Ohkuma, M. Konishi, K. Matsumoto, T. Oki and Y. Hoshino It is certified that error appears in the above-identified patent and that said Letters Patent is hereby corrected as shown below:

Please correct structure in column 9: to appear as shown below.

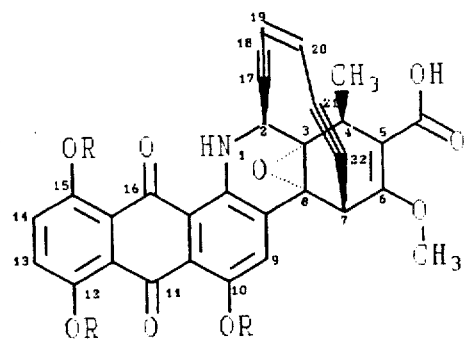

UNITED STATES PATENT AND TRADEMARK OFFICE
CERTIFICATE OF CORRECTION

PATENT NO. : 4,952,572

DATED : August 28, 1990

INVENTOR(S) : H. Ohkuma, M. Konishi, K. Matsumoto, T. Oki and Y. Hoshino

It is certified that error appears in the above-identified patent and that said Letters Patent is hereby corrected as shown below:

Please correct structure in column 11: to appear as shown below.

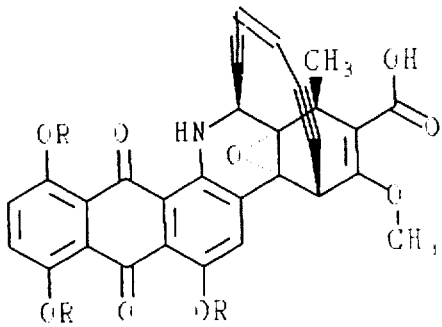

Signed and Sealed this

Seventh Day of January, 1992

Attest:

HARRY F. MANBECK, JR.

Attesting Officer

Commissioner of Patents and Trademarks